United States Patent [19]

Hase et al.

[11] 4,128,636
[45] Dec. 5, 1978

[54] COSMETIC EMULSIONS CONTAINING COPOLYMERS OF 2-HYDROXY-3-HYDROXYALKYL-AMINO-PROPYL(METH)ACRYLATES AND ALKYL (METH)ACRYLATES

[75] Inventors: Brigitte Hase, Erkrath; Joachim Galinke, Langenfeld; Bernd Wegemund, Haan, all of Fed. Rep. of Germany

[73] Assignee: Henkel Kommanditgesellschaft auf Aktien, Düsseldorf-Holthausen, Fed. Rep. of Germany

[21] Appl. No.: 773,608

[22] Filed: Mar. 2, 1977

[30] Foreign Application Priority Data

Mar. 26, 1976 [DE] Fed. Rep. of Germany ....... 2612886

[51] Int. Cl.$^2$ ........................................... A61K 31/78
[52] U.S. Cl. .................................................... 424/81
[58] Field of Search .......... 424/81; 260/23 R, 28.5 R, 260/29.6 R

[56] References Cited

U.S. PATENT DOCUMENTS

| 3,574,822 | 4/1971 | Shepherd et al. | 424/81 |
|---|---|---|---|
| 3,577,517 | 5/1971 | Kubot et al. | 424/81 |
| 3,577,518 | 5/1971 | Shepherd et al. | 424/81 |
| 3,728,314 | 4/1973 | Blank | 424/81 |
| 3,755,560 | 8/1973 | Dickert et al. | 424/81 |
| 3,914,405 | 10/1975 | Shepherd et al. | 424/81 |
| 3,927,199 | 12/1975 | Micchelli et al. | 424/81 |
| 3,927,203 | 12/1975 | Seymour et al. | 424/81 |

FOREIGN PATENT DOCUMENTS 2116787 10/1971 Fed. Rep. of Germany.

Primary Examiner—Donald B. Moyer
Attorney, Agent, or Firm—Hammond & Littell

[57] ABSTRACT

Water-in-oil emulsions containing from 2 to 20% by weight of polymeric emulsifiers comprising statistical copolymers composed of units of the general formulae

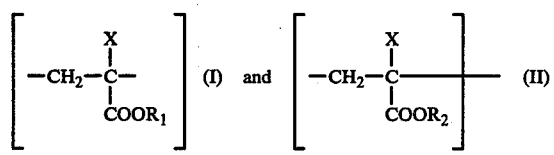

in the molar ratio of (I) to (II) of 2:1 to 20:1; wherein X is hydrogen or methyl, $R_1$ is alkyl having 6 to 24 carbon atoms and $R_2$ is

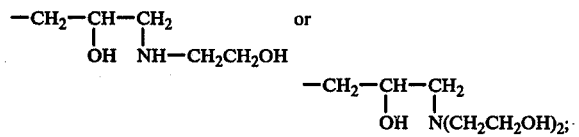

20 to 75% by weight of water; and the remainder to 100% by weight of conventional oily substances used in cosmetic emulsions.

10 Claims, No Drawings

COSMETIC EMULSIONS CONTAINING COPOLYMERS OF 2-HYDROXY-3-HYDROXYALKYL-AMINO-PROPYL(METH)ACRYLATES AND ALKYL (METH)ACRYLATES

FIELD OF THE INVENTION

The invention relates to cosmetic emulsions of the water-in-oil type having a content of statistical copolymers of 2-hydroxy-3-mono- or bis-(2-hydroxyethyl)-amino-propyl (meth)acrylates with alkyl (meth)acrylates as emulsifiers. The invention includes the emulsions themselves and methods for the preparation thereof.

RELATED ART

In contrast to the production of oil-in-water emulsions, only a limited number of emulsifying agents are available for producing cosmetic emulsions of the water-in-oil type and, moreover, the best of these emulsifying agents are becoming increasingly scarce. Even nowadays, wool fat and its derivatives are still some of the most important bases for emulsifying agents for producing creams of the water-in-oil type. However, despite their uncontested advantages, wool fat and its derivatives, such as lanolin, have certain disadvantages. Thus, conventional water-in-oil emulsifying agents based on wool fat and its derivatives impart a strong characteristic odor to the creams prepared with these substances. This in turn, requires strong perfuming which frequently cannot be tolerated by persons having sensitive skin. However, this influencing of the quality of the cream by a strong characteristic odor is not only peculiar to wool fat and its derivatives, but also extends to lanolin-free water-in-oil emulsifying agents based on animal sterols, particularly such emulsifying agents based on cholesterol. Furthermore, low-molecular weight emulsifying agents, together with the effective substances of the cream, can be absorbed by the skin, which is not desirable in all cases.

In addition to the said emulsifying agents based on wool fat, wax alcohols and sterols, the most widely known water-in-oil emulsifiers for cosmetic purposes include the oleic acid esters of various polyols, such as glycerine, pentaerythritol, trimethylolpropane and sorbitol. However, due to the unsaturated character in their acid component, the oleic acid esters have various disadvantages with respect to their technical use, so that there is a genuine need for new and suitable water-in-oil emulsifying agents.

OBJECTS OF THE INVENTION

One object of the present invention is the development of a cosmetic emulsion or cream of the water-in-oil type which can be prepared easily and safely from inexpensive materials without need for costly emulsifying equipment.

Another object of the invention is the development of a cosmetic emulsion of the above type which is substantially odorless and which, therefore, can find general acceptance when containing only a small and harmless amount of perfume.

A particular object of the invention is the production of a cosmetic emulsion of the above type comprising (1) from 2% to 20% by weight of a polymeric emulsifier capable of forming water-in-oil emulsions composed of units of the general formulae

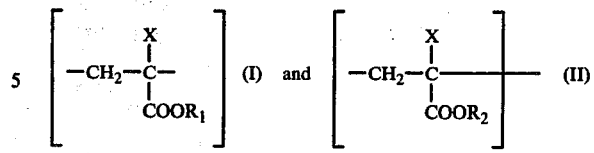

in the molar ratio of (I) to (II) of 2:1 to 20:1, wherein X is hydrogen or methyl, $R_1$ is alkyl having 6 to 24 carbon atoms and $R_2$ is

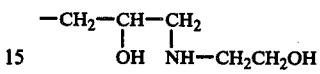

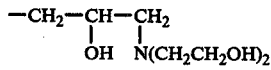

(2) from 20 to 75% by weight of water; and (3) the remainder to 100% by weight of conventional oily substances used in cosmetic emulsions.

These and other objects of the present invention will become more apparent as the description thereof proceeds.

DESCRIPTION OF THE INVENTION

It has now been discovered that the objectionable features of the prior art emulsifiers have been overcome and the above objects have been achieved by the discovery of cosmetic emulsions of the water-in-oil type containing (1) from 2% to 20% by weight, relative to the total weight of the emulsion, of statistical copolymers which are composed, in the molar ratio of (I) to (II) of 2:1 to 20:1, preferably of 3:1 to 12:1, of units of the general formulae

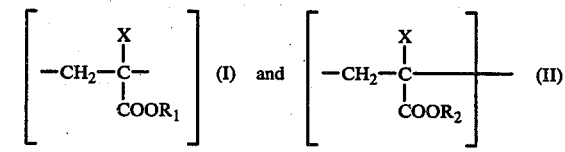

in which X is hydrogen or a methyl radical, $R_1$ is an alkyl radical having 6 to 24 carbon atoms, and $R_2$ is the radical

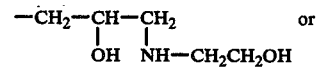

or

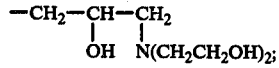

(2) from 20% to 75% by weight of water, relative to the total weight of the emulsion, and (3) the remainder to 100% by weight of conventional oily substances used in cosmetic emulsions, such as vegetable or animal fats, waxes, fatty alcohols, hydrocarbons and further auxiliary substances conventionally used in cosmetic emulsions.

The copolymers of alkyl(meth)acrylates and glycidyl(meth)acrylate, which act as intermediates in the invention, can be manufactured in a generally known manner in one processing step under the conventional conditions of radical polymerization. Polymerization can be effected in nonpolar solvents such as benzene or toluene or in polar solvents such as dioxane, methyl ethyl ketone or tetrahydrofuran, by means of peroxides such as dibenzoyl peroxide or lauroyl peroxide and azo compounds such as azobisisobutyronitrile acting as a catalyst.

Technical production is effected to best advantage in the form of solution polymerization in solvents which dissolve only the monomers but do not dissolve the polymers produced (precipitation polymerization), especially since this results in satisfactorily precipitable polymers which are virtually free from monomers (J. Scheiber, Chemie und Technologie der künstlichen Harze, Volume I, pages 362 ff, 1961).

Glycidyl acrylate and glycidyl methacrylate serve as monomeric starting compounds from which polymer units (II) of the copolymers of the invention are derived after suitable treatment with mono-or diethanolamine. These two monomeric compounds are commercially available.

The monomeric starting compounds from which the polymer units (I) of the copolymers of the invention are derived have the formula

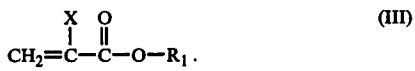

(III)

wherein X is hydrogen or methyl, and $R_1$ is an alkyl radical having 6 to 24, more preferably 8 to 14, carbon atoms.

Among the monomeric starting compounds of the formula (III) above may be mentioned hexyl acrylate, octyl acrylate, 2-ethylhexyl acrylate, nonyl acrylate, decyl acrylate, lauryl acrylate, myristyl acrylate, cetyl acrylate, stearyl acrylate, behenyl acrylate, hexyl methacrylate, octyl methacrylate, nonyl methacrylate, decyl methacrylate, lauryl methacrylate, myristyl methacrylate, cetyl methacrylate, stearyl methacrylate, and behenyl methacrylate.

Among the preferred monomers of the formula (III) having 8 to 14 carbon atoms in the alkyl radical are octyl acrylate, nonyl acrylate, decyl acrylate, lauryl acrylate, myristyl acrylate, octyl methacrylate, nonyl methacrylate, decyl methacrylate, lauryl methacrylate, and myristyl methacrylate.

In order to produce the statistical copolymers, which are used as emulsifying agents in the cosmetic emulsions of the invention, having the units (I) and (II), wherein the radical $R_2$ in the unit (II) is

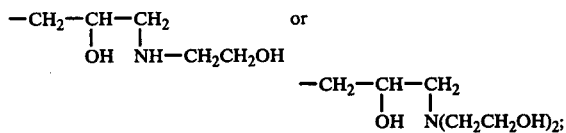

the copolymers obtained in a known manner by radical polymerization of alkyl(meth)acrylates and glycidyl (meth) acrylates (described above) are reacted with equimolar quantities, relative to the oxirane ring, of monoethanolamine and diethanolamine, respectively. An excess of alkanolamine may also be used in order to improve the yield. Reaction can be effected in a generally known manner at suitably high temperature, wherein the alkalinity of the alkanolamines to be reacted is sufficient to catalyse the reaction.

Among the copolymers of the invention may be mentioned 2-hydroxy-3-bis-(2-hydroxyethyl)-aminopropyl acrylate/dodecyl acrylate (1:4 molar ratio); 2-hydroxy-3-(2-hydroxyethyl) aminopropyl acrylate/dodecyl acrylate (1:4 molar ratio); 2-hydroxy-3-(2-hydroxyethyl) aminopropyl acrylate/octyl acrylate (1:8 molar ratio); 2-hydroxy-3-bis-(2-hydroxyethyl) aminopropyl methacrylate/octyl acrylate (1:6 molar ratio); and 2-hydroxy-3-bis-(2-hydroxyethyl) aminopropyl methacrylate/decyl methacrylate (1:4 molar ratio). Very satisfactory results have been obtained using 2-hydroxy-3-bis-(2-hydroxyethyl)-aminopropyl acrylate/dodecyl acrylate (1:4 molar ratio) as the polymeric emulsifier.

In the copolymers of the present invention the molar ratios of the monomer units 2-hydroxy-3-hydroxyethyl-aminopropyl(meth)acrylate: alkyl(meth)acrylate are 1:2 to 1:20, preferably 1:3 to 1:12.

The statistical copolymers of the present invention have average molecular weights between 2,000 and 100,000. Those having average molecular weights between 3,000 and 20,000 are particularly suitable in view of the easy processability and the quality of the emulsions obtained. These molecular weights can be adjusted in a known manner by the amount of catalyst, the nature and amount of the solvent, and by the addition of polymerization regulators.

The emulsions in accordance with the invention are produced in a simple and known manner by dissolving the copolymers, acting as the emulsifying agents, in the oil phase at a temperature of approximately 60° C. to 70° C. Subsequently, the desired quantity of water heated to approximately 60° C. to 65° C. is added, and the emulsion obtained is stirred while cooling.

Cosmetically effective amounts of further constituents of the cosmetic emulsions being manufactured, such as skin moisture regulators, vegetable extracts of effective substances, vitamins, hormones, pigments, salts, perfume oils, UV filtering substances, dyestuffs, etc., are advantageously dissolved or distributed in the phase which absorbs these substances to best advantage. The quantity of emulsifying agent required is 2% to 20% by weight, preferably 5% to 10% by weight, relative to the total cosmetic emulsion. The amount of water to be incorporated can be 20% to 75% by weight, preferably 45% to 65% by weight, relative to the total cosmetic emulsion.

Products conventionally used, such as animal and vegetable oils and fats, synthetic esters of fatty acids with aliphatic alcohols, higher fatty alcohols, waxes, so-called mineral fats and oils, such as paraffin oil, "Vaseline" ®, ceresine, silicone oils and silicone fats are suitable as the oily phase of the cosmetic emulsions in accordance with the invention.

The invention thus also includes a composition which when agitated with water forms a cosmetic emulsion of the water-in-oil type, comprising (1) from 2% to 20% by weight, relative to the total weight of said composition, of a polymeric emulsifier which is a copolymer composed, in the molar ratio of (I) to (II) of 2:1 to 20:1, of units of the general formulae

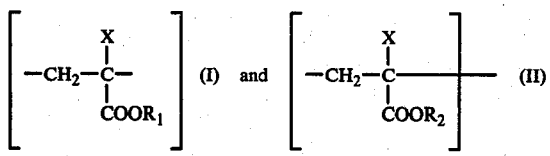

in which X is hydrogen or a methyl radical, $R_1$ is an alkyl radical having 6 to 24 carbon atoms, and $R_2$ is the radical

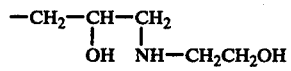

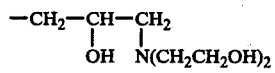

and (2) the remainder to 100% by weight of the composition of conventional oily substances used in cosmetic emulsions. Such conventional oily substances include vegetable and animal oils and fats, synthetic esters of fatty acids with aliphatic alcohols, higher fatty alcohols, waxes, so-called mineral fats and oils, such as paraffin oil, "Vaseline" ®, ceresin, silicone oils and silicone fats. In addition the cosmetic emulsions or creams can contain, if desired, other auxiliary substances normally used in cosmetic emulsions. Examples of such auxiliary substances are skin moisture regulators, vegetable extracts of effective substances, vitamins, hormones, pigments, salts, perfume oils, UV filtering substances, dyestuffs, etc.

German Offenlegungsschrift (DOS) No. 2,116,787 has already described the use of water-in-oil emulsifying agents in the form of sequence polymers which at the same time have at least one lipophilic sequence and one hydrophilic sequence. Each sequence should have the properties of the corresponding homopolymer. These sequence polymers are obtained by anionic polymerization which places high demands on the purity of the substances used, and requires working at low temperatures under a protective gas and increased safety precautions when handling spontaneously combustible catalysts. In contrast to this, the emulsifying agents required for producing the emulsions in accordance with the present invention can be manufactured in a simple manner.

In general, the emulsions in accordance with the present invention can also be used by persons having a sensitive skin. Since they do not have any appreciable characteristic odor, they do not require heavy perfuming, which, in turn, has an advantageous effect upon the compatibility and also reduces costs. Furthermore, a very advantageous property of the emulsions in accordance with the invention is their high resistance to temperature, which enables them to withstand a thermal stress of 50° C. for a period of 6 weeks without any detrimental effect.

In the specification and claims, the term "(meth)acrylate(s)" is used to designate ester(s) of acrylic acid and ester(s) of methacrylic acid.

The following Examples are intended to further explain the invention, but without limiting the invention to these Examples.

EXAMPLES

The following example illustrates the preparation of a copolymer for use in the cosmetic emulsions of the present invention.

EXAMPLE 1

A. Glycidyl acrylate/dodecyl acrylate copolymer (1:4 molar ratio) (intermediate product)

A solution of 10.24 gm (0.08 mole) of glycidyl acrylate, 76.8 gm (0.32 mole) of dodecyl acrylate and 1.76 gm of dibenzoyl peroxide in 127 gm of toluene was added, drop by drop, at 80° C. within one hour to a solution of 2.56 gm (0.02 mole) of glycidyl acrylate, 19.2 gm (0.08 mole) of dodecyl acrylate and 0.44 gm of dibenzoyl peroxide (acting as a catalyst) in 127 gm of toluene. The reaction mixture was subsequently stirred for a further 5 hours at 80° C. After the reaction had ended, the solvent was distilled off and the copolymer obtained was washed a few times with methanol. 96 gm (88% of theory) of glycidyl acrylate/dodecyl acrylate copolymer (1:4 molar ratio) were obtained.

The other glycidyl acrylate/alkyl(meth)acrylate copolymers of the invention which act as an intermediate product were produced in an analogous manner to the above copolymer, and the glycidyl methacrylate/alkyl(meth)acrylate copolymers were similarly produced in an analogous manner using glycidyl methacrylate instead of glycidyl acrylate.

B. 2-hydroxy-3-bis-(2-hydroxyethyl)-aminopropyl acrylate/dodecyl acrylate copolymer (1:4 molar ratio)

Product of reaction of glycidyl acrylate/dodecyl acrylate copolymer (1:4 molar ratio) with diethanolamine.

42 gm (0.1 mole) of diethanolamine were added to a solution of 108.8 gm of glycidyl acrylate/dodecyl acrylate copolymer (1:4 molar ratio) (0.1 mole relative to glycidyl acrylate) in 435 gm of dioxane, and the reaction mixture was stirred for 6 hours at 80° C. The reaction product was subsequently precipitated by means of methanol and was washed several times with methanol. 128 gm (85% of theory) of 2-hydroxy-3-bis-(2-hydroxyethyl)-aminopropyl acrylate/dodecyl acrylate copolymer (1:4 molar ratio) were obtained.

The other 2-hydroxy-3-hydroxyalkylaminopropyl (meth)acrylate/alkyl(meth)acrylate copolymers, used in the examples given below, were produced in an analogous manner to the above method.

EXAMPLE 2

Cosmetic emulsion based on Vaseline ®

A mixture of 10 gm of 2-hydroxy-3-bis-(2-hydroxyethyl)-aminopropyl acrylate/dodecyl acrylate copolymer (1:4 molar ratio) and 40 gm of Vaseline ® were melted together by heating to 65° C. 50 gm of water, heated to 65° C., were added to the melt, and the mass was allowed to cool under constant stirring. The emulsion can be readily produced by manual stirring. The cream obtained is stable for several months and did not exhibit any change even after 6 weeks at 50° C. This basic cream can be used to manufacture various skin creams by adding various conventional cosmetic agents and perfume oils.

The 2-hydroxy-3-bis-(2-hydroxyethyl)amino-propyl acrylate/dodecyl acrylate copolymer (1:4 molar ratio) may be replaced in the foregoing example with equally satisfactory results by, for example, the following copolymers:

| Copolymer | Molar Ratio |
|---|---|
| 2-hydroxy-3-(2-hydroxyethyl)aminopropyl acrylate/dodecyl acrylate | (1:4) |
| 2-hydroxy-3-(2-hydroxyethyl)aminopropyl acrylate/octyl acrylate | (1:8) |
| 2-hydroxy-3-(2-hydroxyethyl)aminopropyl acrylate/stearyl acrylate | (1:2) |
| 2-hydroxy-3-(2-hydroxyethyl)aminopropyl methacrylate/octyl acrylate | (1:6) |
| 2-hydroxy-3-(2-hydroxyethyl)aminopropyl methacrylate/cetyl methacrylate | (1:3) |
| 2-hydroxy-3-bis-(2-hydroxyethyl)aminopropyl methacrylate/octyl acrylate | (1:6) |
| 2-hydroxy-3-bis-(2-hydroxyethyl)aminopropyl methacrylate/decyl methacrylate | (1:4) |

EXAMPLE 3

Cosmetic emulsion based on peanut oil/decyl oleate mixture

A mixture of 4 gm of 2-hydroxy-3-bis-(2-hydroxyethyl) aminopropyl acrylate/dodecyl acrylate copolymer (1:4 molar ratio), 40 gm of a hardened peanut oil/decyl oleate mixture (90:10 by weight), 3 gm of beeswax, and 3 gm of glyceryl monooleate was melted together by heating to 70° C. 50 gm of water, heated to 65° C., were added to the melt under constant stirring, and the mass was allowed to cool under further stirring. A cream was obtained having stability properties largely similar to those of the cream of Example 2. Various skin creams can be prepared from this basic cream by incorporating additional cosmetically effective amounts of conventional cosmetically effective substances, such as skin moisture regulators, vegetable extracts, and perfume oils. The 2-hydroxy-3-bis-(2-hydroxyethyl) aminopropyl acrylate/dodecyl acrylate copolymer (1:4 molar ratio) can be replaced with equally good results by, for example, the following copolymers:

| Copolymer | Molar Ratio |
|---|---|
| 2-hydroxy-3-(2-hydroxyethyl) aminopropyl acrylate/dodecyl acrylate | (1:4) |
| 2-hydroxy-3-(2-hydroxyethyl) aminopropyl acrylate/octyl acrylate | (1:8) |
| 2-hydroxy-3-bis-(2-hydroxyethyl) aminopropyl acrylate/octyl acrylate | (1:8) |

EXAMPLE 4

Cosmetic emulsion based on Vaseline ®/decyl oleate mixture

A mixture of 7 gm of 2-hydroxy-3-bis-(2-hydroxyethyl) aminopropyl acrylate/dodecyl acrylate copolymer (1:4 molar ratio), 10 gm of Vaseline ®, 15 gm of decyl oleate, 3 gm of beeswax, and 2 gm of calcium stearate was melted together by heating to 65° C. 63 gm of water, heated to 65° C., were stirred into this mixture and stirring was continued until the emulsion had cooled. A cream was obtained whose stability properties are largely similar to those of the two above-mentioned creams. A large number of cosmetic creams based on this basic cream can be produced by incorporating conventional cosmetically effective substances and perfume oils.

The 2-hydroxy-3-bis-(2-hydroxyethyl) aminopropyl acrylate/dodecyl acrylate copolymer (1:4 molar ratio) can be replaced with equally good results by the same quantity of 2-hydroxy-3-bis-(2-hydroxyethyl) aminopropyl acrylate/octyl acrylate copolymer (1:8 molar ratio), 2-hydroxy-3-(2-hydroxyethyl) aminopropyl acrylate/dodecyl acrylate copolymer (1:4 molar ratio), 2-hydroxy-3-(2-hydroxyethyl) aminopropyl acrylate/octyl acrylate copolymer (1:8 molar ratio) and the other copolymer of the invention.

EXAMPLE 5

Cosmetic emulsions based on hardened peanut oil

A mixture of 6 gm of 2-hydroxy-3-bis-(2-hydroxyethyl) aminopropyl acrylate/dodecyl acrylate copolymer (1:4 molar ratio) and 44 gm of hardened peanut oil was melted together by heating to 65° C. 50 gm of water, heated to 65° C., were stirred into this mixture. After stirring until cold, a cream was obtained whose stability properties are largely similar to those of the above-mentioned creams. The cream can act as a basic cream for various cosmetic preparations, such as described above.

We claim:

1. A cosmetic emulsion of the water-in-oil type, comprising (1) from 2% to 20% by weight of statistical copolymers which are composed, in the molar ratio of (I) to (II) of 2:1 to 20:1, of units of the general formulae $$\left[ -CH_2-\underset{\underset{COOR_1}{|}}{\overset{\overset{X}{|}}{C}}- \right] \quad (I) \quad \text{and} \quad \left[ -CH_2-\underset{\underset{COOR_2}{|}}{\overset{\overset{X}{|}}{C}}- \right] \quad (II)$$

wherein X is hydrogen or a methyl radical, $R_1$ is an alkyl radical of 6 to 24 carbon atoms, and $R_2$ is a radical selected from the group consisting of $$-CH_2-\underset{\underset{OH}{|}}{CH}-\underset{\underset{NH-CH_2CH_2OH}{|}}{CH_2} \quad \text{and}$$

$$-CH_2-\underset{\underset{OH}{|}}{CH}-\underset{\underset{N(CH_2CH_2OH)_2}{|}}{CH_2}$$

(2) from 20% to 75% by weight of water, and (3) the remainder to 100% by weight of conventional oily substances used in cosmetic emulsions.

2. The cosmetic emulsion of claim 1 wherein $R_1$ is an alkyl radical of 8 to 14 carbon atoms.

3. The cosmetic emulsion of claim 1 wherein the polymeric emulsifier has an average molecular weight of from 2,000 to 100,000.

4. The cosmetic emulsion of claim 3 wherein the average molecular weight is from 3,000 to 20,000.

5. The cosmetic emulsion of claim 1 wherein the polymeric emulsifier is present in an amount of from 5% to 10% by weight, relative to the total cosmetic emulsion.

6. The cosmetic emulsion of claim 5 wherein the water is present in an amount of from 45% to 65% by weight, relative to the total cosmetic emulsion.

7. The cosmetic emulsion of claim 1 wherein, in addition to the polymeric emulsifier and water, there are present vegetable or animal fats, waxes, fatty alcohols and hydrocarbons as said oily substances.

8. In the method of producing a cosmetic emulsion of the water-in-oil type comprising mixing an emulsifier capable of forming water-in-oil creams with a cosmetically acceptable oily material at elevated temperatures, mixing therewith from 20% to 75% by weight of water, cooling under agitation and recovering said cosmetic emulsion of the water-in-oil type, the improvement consisting of adding (1) from 2% to 20% by weight of the statistical copolymer of claim 1, (2) from 20% to 75% by weight of water and (3) the remainder to 100% by weight of conventional oily substances used on cosmetic emulsions.

9. A composition which when agitated with water forms a cosmetic emulsion of the water-in-oil type, comprising (1) from 2% to 20% by weight of the statistical copolymer of claim 1, and (2) the remainder to 100% by weight of the composition of conventional oily substances used in cosmetic emulsions.

10. The cosmetic emulsion of claim 1 wherein the molar ratio of (I) to (II) is 3:1 to 12:1.

* * * * *